Jan. 22, 1974 B. J. MACHIN Plant Pat. 3,446
CHRYSANTHEMUM PLANT
Filed Dec. 27, 1971
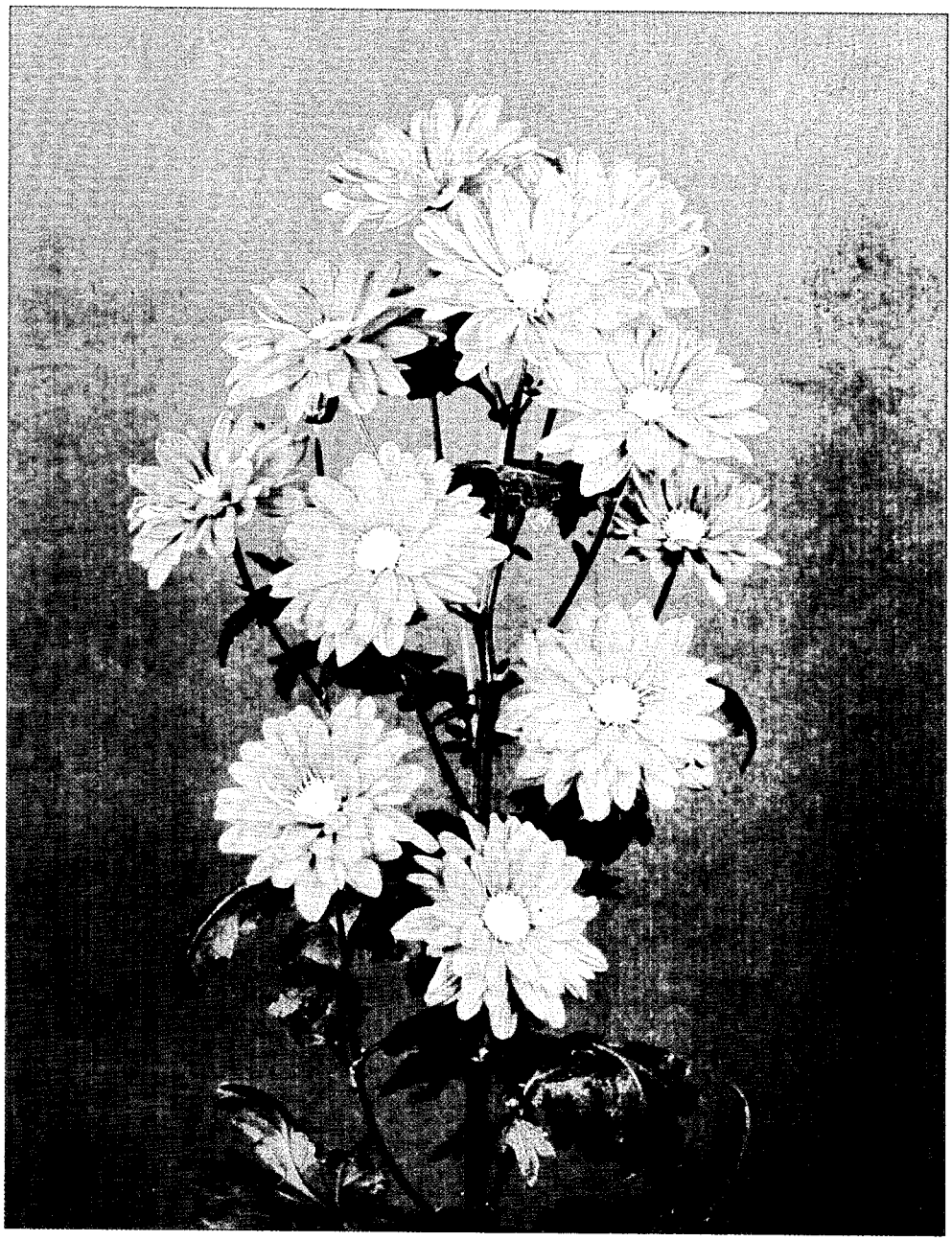

United States Patent Office

Plant Pat. 3,446
Patented Jan. 22, 1974

3,446
CHRYSANTHEMUM PLANT

Barrie John Machin, East Broyle Estate, Chichester, England, assignor to Frampton's Nurseries Limited, Chichester, Sussex, England Filed Dec. 27, 1971, Ser. No. 212,832
Int. Cl. A01h *5/00*
U.S. Cl. Plt.—74 1 Claim This invention relates to a new and distinctive variety of *Chrysanthemum morifolium* Bailey (spray type) known as Red Nero.

Red Nero is a sport from the variety Nero (unpatented) which is a seedling originated by me from a cross made in 1967 between the variety Tuneful and the variety Delight, both unpatented, the former being the seed parent, the latter being the pollen parent.

The variety Nero resulted from an extensive breeding program with the object of producing improved varieties for year-round chrysanthemum production programs with more vigor and reduced flowering time as compared with existing varieties. The immediate objective was to improve the varieties Tuneful and Delight (both unpatented) which in Southern England required a total of 13 or 14 weeks for single stem flowering during the summer.

The variety Red Nero is a sport induced by irradiation from Nero in October 1969, in cultivated ground at Frampton's Nurseries Ltd., Forbridge Nursery, Chichester, Sussex, England.

Red Nero is distinguished from Nero by the fact that its color is distinctly deeper, RHS 46B Currant Red, as against red bronze, RHS 42B, in the case of Nero.

Red Nero is distinguished from the related variety Red Delight by the following improved characteristics.

(1) It is extremely vigorous and will produce flowering crops in 12 weeks from rooted cuttings during the summer and 16 weeks from rooted cuttings during the winter.
(2) Despite its extreme vigor it is also responsive and will set buds and flower uniformly in a wide range of environmental conditions.
(3) Its color is currant red comparing very favorably with other red bronze singles, e.g., Red Delight, and holding well in high temperature conditions.

Asexual reproduction of this new variety Red Nero, as performed in Sussex, England, by rooting vegetative shoots, shows that the above characteristics are fixed and come true to type through succeeding generations.

The accompanying drawing shows a typical flower of my new variety in color as nearly true as it is reasonably possible to make the same in a color illustration of this character.

The following is a detailed description of the new variety Red Nero with color terminology in accordance with the Royal Horticultural Society color chart, hereinafter referred to as RHS.

Genus: Chrysanthemum
Species: *Morifolium* Bailey
Type: Spray
Class: Single
Breeding: The original Nero seedling resulted from a cross between the variety Tuneful, the seed parent, and Delight, the pollen parent. The cross was made in 1967 at Frampton's Nurseries Ltd., Forbridge Nursery, Chichester, Sussex, England.
Propagation: Holds its distinguishing characteristics through succeeding propagations by rooting vegetative shoots.
Flower: When grown and observed in Sussex, England, 6 to 12 flowers are borne on pedicels after removal of the main apical bud.
Bloom:
*Size.*—Average diameter is 10 cm. when fully open.
*Petalage.*—Single—approximately 50 ray petals. Diameter of disc is 1¾ to 2 cm.
*Form.*—Single with flat slightly reflexing petals.
*Petals.*—Long, broad, overlapping, blunt and with medium texture.
*Pedicels.*—Thick and 10 to 12 cm. in length.
Color of open bloom:
Inner face of fully expanded ray petal, RHS 36B.
Outer face of fully expanded ray petal, RH 20B.
Inner face of young ray petal, RHS 46A.
Outer face of young ray petal, RHS 20B.
Inner and outer faces of disc petals, RHS 7A.
Response Group: 10 weeks.
Temperature tolerance: 55–60° F. at night.
Plant: Strong upright habit of growth.
Foliage: Medium quality, average internode length, 3 cm.
Medium to large size.
Color, RHS 137B.
Texture, medium.
Stem: Thick and strong, with color 143C at flowering; water uptake, good.

I claim:

1. A new and distinct variety of *Chrysanthemum morifolium* Bailey, substantially as herein shown and described, characterized particularly as to novelty by the unique combination of reduced flowering time, uniform response in a wide range of environmental conditions, and currant red color.

No references cited.

ROBERT E. BAGWILL, Primary Examiner